United States Patent [19]

Wolfe

[11] 4,275,715

[45] Jun. 30, 1981

[54] EAR RACK FOR SUPPORTING DOG EARS ERECT

[76] Inventor: Randall R. Wolfe, Rte. 5, Box 99 W, Jasper, Ala. 35501

[21] Appl. No.: 106,516

[22] Filed: Dec. 26, 1979

[51] Int. Cl.³ .................. A61F 5/08

[52] U.S. Cl. .................. 128/76 R; 119/96

[58] Field of Search .................. 128/87 R, 89 R, 76 R, 128/82, 83; 119/96; 3/1 R

[56] References Cited

U.S. PATENT DOCUMENTS

| | | | |
|---|---|---|---|
| 3,257,990 | 6/1966 | Robertson et al. | 119/96 |
| 3,970,080 | 7/1976 | White | 119/96 |

*Primary Examiner*—John D. Yasko

*Attorney, Agent, or Firm*—Woodford R. Thompson, Jr.

[57] ABSTRACT

An ear rack having a base member of a width to span substantially the distance between the ears of a dog carries an upstanding ear support at each side thereof in position to lie alongside the inner surface of an adjacent dog ear. Each ear support is attachable to a dog ear adjacent thereto to support the ear erect.

7 Claims, 8 Drawing Figures

FIG_1
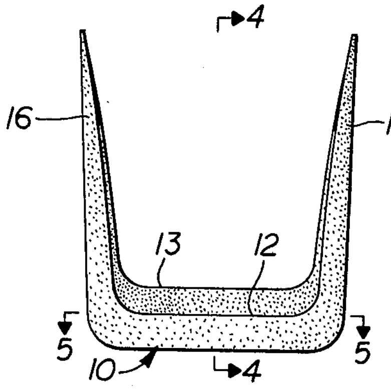
FIG_2
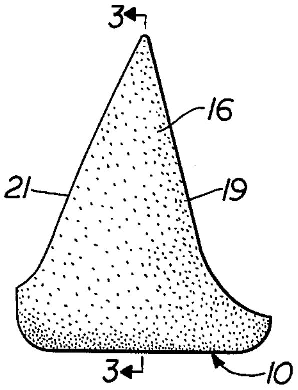
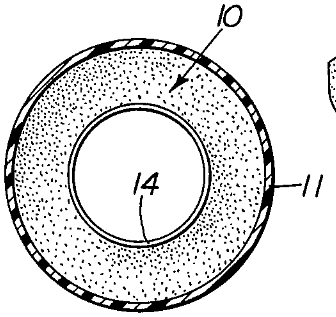
FIG_5
FIG_3
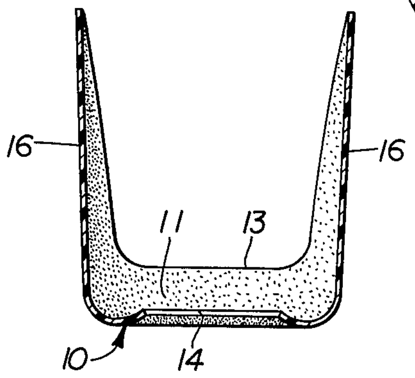
FIG_4
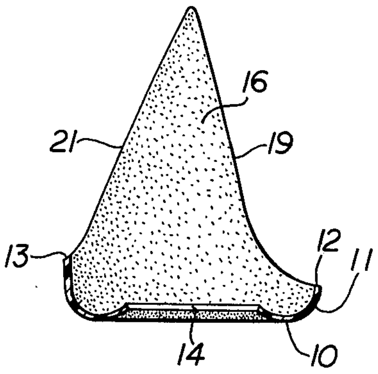
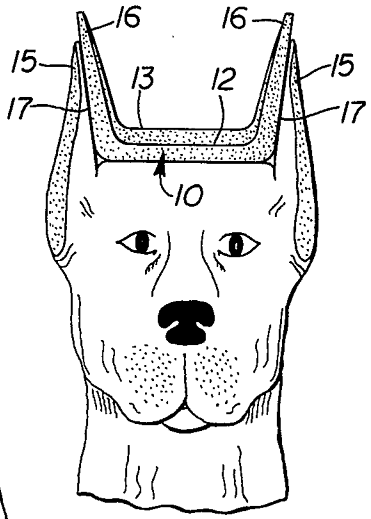
FIG_6
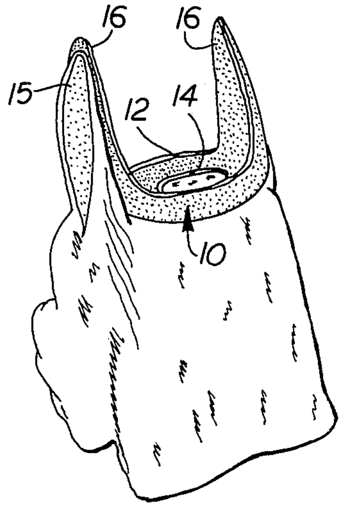
FIG_7
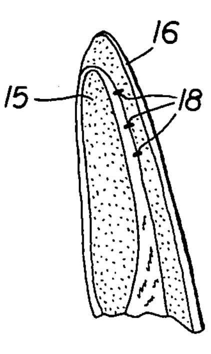
FIG_8

EAR RACK FOR SUPPORTING DOG EARS ERECT

BACKGROUND OF THE INVENTION

This invention relates to an ear rack for supporting dog ears erect and more particularly to a disposable ear support for dogs after ear crop surgery.

As is well known, it is customary that certain dogs, such as Dobermans, Boxers, Schnauzers and Great Danes have their ears cropped at approximately ten to fourteen weeks of age. During the healing process after surgery, the ears should be held erect and protected from injury or self-inflicted trauma. It is very difficult with some methods to keep the ears in racks or bandages until the ears are healed properly. This is especially true in view of the fact that, with fresh cut edges, it is much better to maintain such fresh cut edges open to the air to provide ventilation for drying purposes. Also, prior art devices for retaining dog ears erect after surgery are very difficult to sterilize, are cumbersome to the patient, and are very unsightly in appearance. Furthermore, such prior art devices are quite expensive due to the fact that taping and other racking procedures heretofore employed require a considerable amount of time and materials to install and maintain the rack in place.

SUMMARY OF THE INVENTION

In accordance with my invention, I provide an ear rack for supporting dog ears erect whereby the ears are trained to remain in this position during the healing process and at the same time the fresh cut ear edges are exposed to the air whereby they will dry and heal quicker. Also, the fresh cut ear can be medicated without bandaging and where hemorrhaging does occur, bandaging over my improved ear rack and the dog ear is easy and quick.

My improved ear rack embodies a base member which spans substantially the distance between the ears of a dog and carries upstanding ear support members at each side thereof which are adapted to lie alongside the inner surface of an adjacent dog ear with each ear support being attachable to the dog ear adjacent thereto. Preferably, the ear rack is formed of a disposable material which is easy to sterilize, such as plastic or the like. My improved ear rack is simple of construction, economical of manufacture, light in weight and requires a minimum of time and effort to install and keep in place. Accordingly, after healing occurs and the stitches are removed, the owner of the dog can continue the use of my improved ear rack to maintain the dog's ears in an erect position indefinitely until the ears stand without the aid of the ear rack. My improved ear rack can also be formed of a size and shape to project beyond the edges of a small size ear whereby the upstanding support members are adapted to fit a larger size ear and can be trimmed to fit selected smaller size ears.

DESCRIPTION OF THE DRAWING

An ear rack embodying features of my invention is illustrated in the accompanying drawing, forming a part of this application, in which:

FIG. 1 is a front elevational view of the ear rack;

FIG. 2 is a side elevational view thereof;

FIG. 3 is a vertical sectional view taken generally along the line 3—3 of FIG. 2;

FIG. 4 is a sectional view taken generally along the line 4—4 of FIG. 1;

FIG. 5 is a horizontal sectional view taken generally along the line 5—5 of FIG. 1;

FIG. 6 is a front elevational view, drawn to a smaller scale, and showing the ear rack mounted on the head of a dog;

FIG. 7 is a perspective view showing the ear rack installed on the head of a dog and looking from the rear; and, FIG. 8 is a fragmental view showing one of the upstanding support members attached to the ear of a dog by sutures.

DETAILED DESCRIPTION

Referring now to the drawing for a better understanding of my invention, my improved ear rack comprises a horizontal base member 10 which is preferably generally round, as viewed in plan. Formed integrally with the base member 10 is an upstanding flange 11 which extends around the periphery of the base member, as shown in FIG. 5. As shown in FIGS. 1 and 4, the front portion 12 of the upstanding flange 11 is lower than the rear portion 13 thereof so as to reduce the overall height of the rack adjacent the front of the dog's head and thereby reduce the chances of the ear rack interfering with free movement of the dog's head.

As shown in FIGS. 3, 4, 5 and 7, the central portion of the base member 10 is removed so as to provide a centrally disposed opening 14 therethrough which facilitates support of the base member on the head of a dog. As shown in FIGS. 6 and 7, the base member 10 is of a width to span substantially the distance between the ears 15 of a dog. An upstanding support member 16 is carried by each side of the base member 10 in position for the outer surface thereof to lie alongside the inner surface of the dog ear 15 adjacent thereto. As shown in FIGS. 3 and 4, the upstanding support members 16 are formed integrally with the upstanding flange 11 of the base member 10 at each side of the base member to provide a study support or connection between the upstanding members 16 and the base member 10. Each upstanding support member 16 is secured to the dog ear adjacent thereto whereby each dog ear 15 is supported in an erect position, as shown in FIGS. 6 and 7. In actual practice, I have found that the upstanding support members 16 may be secured to the inner surfaces of the ears 15 adjacent thereto by various means, such as by applying an adhesive 17 between the outer surface of the upstanding support member 16 and the ear 15 adjacent thereto, as shown in FIG. 6. In view of the fact that such adhesives are well known in the art and form no part of my invention per se, no further description thereof is deemed necessary.

As shown in FIG. 8, I show the dog ear 15 as being secured to the inner surface of an adjacent upstanding support member 16 by sutures 18. It will be understood, however, that other suitable means may be employed for securing the inner surface of the ear 15 of a dog to the outer surface of an adjacent upstanding support member 16. As shown in FIGS. 2 and 4, each of the upstanding support members 16 is formed of a thin, sheet-like material having a front edge 19 and a rear edge 21 which taper upwardly toward the top of the support member 16 whereby they conform generally to the shape of the dog's ear after being cropped. Preferably, each of the upstanding support members 16 is of a size and shape to project beyond the edges of a smaller size ear so that the upstanding support member 16 is adapted to fit a larger ear and can also be trimmed to fit selected ear sizes. Accordingly, each ear rack would be adapted to fit a plurality of ear sizes by merely trimming the edges 19 and 21 of the upstanding support members 16 to accommodate the ears on which the rack is to be installed. Preferably, the edges 19 and 21 of the upstanding support member 16 project beyond the periphery of the dog's ear 15 so as to protect the fresh cut edges as they go through the healing process. Preferably, the ear rack is formed of a disposable material which is easily sterilized, such as plastic or the like.

From the foregoing, it will be seen that I have devised an improved ear rack for supporting dog ears erect. By providing a base member which spans substantially the distance between the ears of a dog and carries upstanding support members which are in position to lie alongside the inner surfaces of a dog's ear adjacent thereto, the ears of a dog may be easily and quickly attached to the upstanding support members to thereby retain the ears in an erect position and at the same time protect the ear from damage as the fresh cut edges go through the healing process. Also, by providing an ear rack which permits the fresh cut ear edges to be exposed to air, the edges are maintained in a dry condition at all times to thus facilitate healing. Furthermore, by providing an ear rack which may be formed as an integral unit from a plastic-like material, the ear rack is not cumbersome to the dog and at the same time is neat in appearance and is easily maintained in a sanitary condition at all times.

While I have shown my invention in two forms, it will be obvious to those skilled in the art that it is not so limited, but is susceptible of various other changes and modifications without departing from the spirit thereof.

What I claim is:

1. An ear rack for supporting the ears of a dog erect comprising, (a) a generally round base member as viewed in plan of a width to span substantially the distance between the ears of a dog and having an upstanding flange extending around the periphery thereof, (b) an upstanding support member formed integrally with said upstanding flange at each side of said base member in position for the outer surface thereof to lie alongside the inner surface of a dog ear adjacent thereto, and (c) means to secure each said upstanding support member to the dog ear adjacent thereto so that each dog ear is thereby supported in an erect position.

2. An ear rack as defined in claim 1 in which the central portion of said base member is removed to provide a centrally disposed opening therethrough which facilitates support of said base member on the head of a dog.

3. An ear rack as defined in claim 1 in which said upstanding flange at the front of said base member is lower than said upstanding flange at the rear of said base member.

4. An ear rack as defined in claim 1 in which each said upstanding support member is formed of a thin sheet-like material having front and rear edges which taper upwardly toward the top of the upstanding support member.

5. An ear rack as defined in claim 1 in which said upstanding support member is of a size and shape to project beyond the edges of a smaller size ear so that said upstanding support member is adapted to fit a larger size ear and can be trimmed to fit selected ear sizes.

6. An ear rack as defined in claim 1 in which said means to secure each said upstanding support member to the dog ear adjacent thereto comprises sutures.

7. An ear rack as defined in claim 1 in which said means to secure each said upstanding support member to the dog ear adjacent thereto comprises an adhesive.

* * * * *